United States Patent [19]

Hansen et al.

[11] 3,956,924

[45] May 18, 1976

[54] SYSTEM AND METHOD FOR MEASURING MEAT TENDERNESS

[75] Inventors: Leo J. Hansen, Clarendon Hills, Ill.; Harry E. Lockery, Sudbury, Mass.

[73] Assignee: Armour and Company, Phoenix, Ariz.

[22] Filed: Oct. 22, 1971

[21] Appl. No.: 191,841

Related U.S. Application Data

[63] Continuation of Ser. No. 778,551, Nov. 25, 1968, abandoned.

[52] U.S. Cl. .................................................. 73/81
[51] Int. Cl.² ......................................... G01N 3/42
[58] Field of Search .............. 73/81, 88.5 R, 141 A, 73/398 AR

[56] References Cited
UNITED STATES PATENTS

| | | | |
|---|---|---|---|
| 2,775,887 | 1/1957 | Hines | 73/141 A |
| 3,169,394 | 2/1965 | Vosteen et al. | 73/88.5 R |
| 3,197,697 | 7/1965 | McCauley | 73/88.5 R X |
| 3,245,252 | 4/1966 | First et al. | 73/88.5 R |
| 3,289,134 | 11/1966 | Laimins et al. | 73/398 AR X |
| 3,335,381 | 8/1967 | Di Giovanni | 73/141 A X |
| 3,389,432 | 6/1968 | Griesheimer et al. | 73/88.5 R X |
| 3,447,362 | 6/1969 | Pien | 73/141 A X |
| 3,450,978 | 6/1969 | Norman | 73/398 AR X |
| 3,456,226 | 7/1969 | Vick | 73/141 A X |
| 3,593,572 | 7/1971 | Hansen | 73/81 |
| 3,602,038 | 8/1971 | Hansen | 73/81 |

*Primary Examiner*—James J. Gill
*Attorney, Agent, or Firm*—Frank T. Barber; James J. Hill

[57] ABSTRACT

A system for measuring the tenderness of meat includes a probe equipped with a force transducer which generates an electrical signal having an instantaneous amplitude representative of the penetration resistance force encountered by the probe during insertion to a predetermined depth. The transducer is connected in a bridge circuit which is energized by a storage battery coupled to the bridge through a regulating network to insure a constant supply voltage for the resistive transducer. An amplifier receives the force signal and couples it to a memory circuit which includes a capacitor fed by a unidirectional current-carrying circuit. The capacitor stores a charge proportional to incremental increases in the transducer signal; and since it does not discharge except by operator reset, the charge stored after the probe comes to rest is representative of the peak penetration resistance force and, thus, a measure of the tenderness of the meat. A readout circuit generates a visual indication of the voltage across the memory capacitor which may then be discharged by selective action of the operator to set the system for a new measurement.

15 Claims, 3 Drawing Figures

SYSTEM AND METHOD FOR MEASURING MEAT TENDERNESS

This is a continuation application of our copending, co-owned application for "System and Method for Measuring Meat Tenderness", Ser. No. 778,551, filed Nov. 25, 1968, now abandoned.

Reference is made to a, co-owned application, Ser. No. 776,234, for MEASURING THE TENDERNESS OF MEAT FOR DETERMINING ITS TENDERNESS UPON COOKING, filed Nov. 15, 1968, now U.S. Pat. No. 3,593,572 which is a continuation-in-part of application Ser. No. 705,722, filed Feb. 15, 1968, now abandoned, and which discloses in detail a process for testing meat for tenderness.

BACKGROUND AND SUMMARY

The present invention relates to a system for measuring the tenderness of meat; and more particularly it relates to a system for generating an electrical signal representative of the tenderness of the meat and which is a more reliable and more accurate measure of the tenderness of the meat after it is cooked.

Prior tests for determining the tenderness of raw meat which center upon the use of a probe being inserted into the meat have included the use of both blunt probes pressed into the meat and pointed probes (or needles) which sink into the meat under fixed weight or force. In this latter method, the depth to which the probe descends under the fixed weight is taken to be a measure of the tenderness of the meat. This test (the so-called penetrometer test) has been found not to be entirely reliable and satisfactory.

There is described in the above-identified application a method of measuring the tenderness of meat by inserting a probe with spaced needles into the carcass and measuring the peak penetration resistance force, this measurement being a more reliable and more accurate determination of the tenderness of the meat after cooking, and, hence, a more meaningful measurement.

The present invention relates to an electronic system for use in combination with a probe for measuring penetration resistance force. A force transducer is carried by the probe for generating a signal which is representative of the resistive force incurred during penetration to a predetermined depth. Thus, for a complete penetration stroke, there will be a slightly irregular, but generally increasing signal from the time of initial probe insertion until the probe comes to rest at maximum penetration, at which time the resistive force signal returns to zero.

The embodiment described within is a self-contained, portable unit which is not affected by wide variations in ambient temperature as might, for example, be encountered with a usage at normal room temperature followed by usage in a cold storage area. Thus, a plurality of resistive strain gauges comprise the force transducer, and they are incorporated in an electrical bridge circuit which is energized by storage batteries coupled to the bridge circuit through a regulating network to insure a constant supply voltage for the bridge. The bridge supply voltage and resultant force signal are thus independent of the charge on the batteries and the ambient temperature.

A difference amplifier receives the output signal of the bridge circuit and couples it to a memory circuit. A capacitor in the memory circuit is coupled to the output of the difference amplifier by means of a circuit which permits current to flow unidirectionally into the capacitor thereby generating a charge on the capacitor (and corresponding voltage across the capacitor) which is representative of the instantaneous peak amplitude of the transducer signal. Since the capacitor is not allowed to discharge, the charge stored on the capacitor is indicative of the peak resistive force which occured during the penetration stroke; and the voltage across the capacitor then becomes a measure of the tenderness of the carcass.

A readout circuit generates a visual indication (or permanent record, if desired) of the voltage across the memory capacitor. The capacitor may be discharged by the operator's closing a switch which sets the capacitor charge to a reference level for taking a new measurement.

Provision is also made for charging the storage batteries and for modifying the voltage across the storage batteries under a test load so that the charge may be measured with the same scale of the readout apparatus as is used to read the voltage across the memory capacitor.

Other features and advantages of the present invention will be apparent to persons skilled in the art from the following detailed description of a preferred embodiment accompanied by the attached drawing.

THE DRAWING

DETAILED DESCRIPTION

Figure 1:
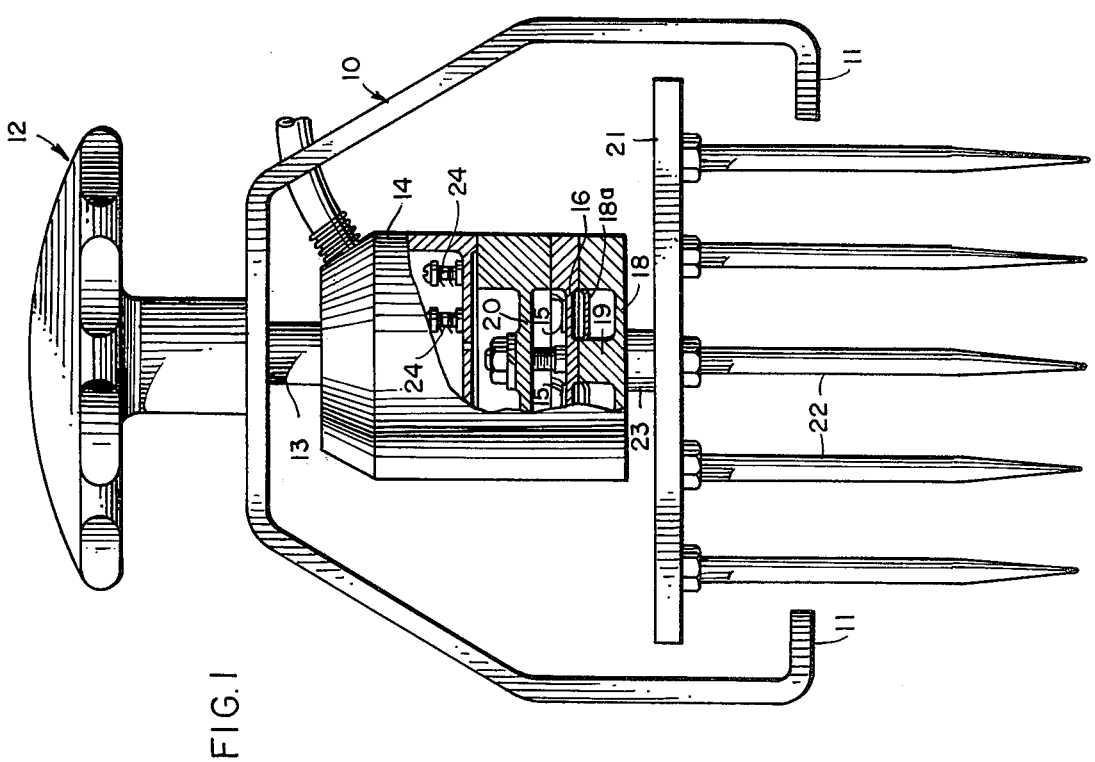
FIG. 1 is a side elevation view, partially cut away, of a preferred embodiment of a probe used in combination with the measuring system of the present invention.

FIG. 1 illustrates a probe preferably used in combination with the inventive measuring system. Referring then to FIG. 1, reference numeral 10 generally designates a frame member in the shape of an inverted U and provided at its bottom with inwardly-turned stop members 11 which limit the penetration stroke of the probe by engaging the carcass. A fixed handle generally designated 12 is secured to the top of the frame 10.

Mounted within the U of the frame 10 and beneath the handle 12 is a support 13 to which there is secured a housing 14 for the force transducer. The transducer used in the illustrated embodiment is in the form of strain gauges or sensors 15 which are mounted on the top of a flexible diaphragm 16 rigidly secured about its periphery to the housing 14. The central portion of the diaphragm 16 is directly connected to the center of a bottom 18 of the housing 14 by means of a shaft 19; and the upward movement of the diaphragm 16 is limited by means of an adjustable bolt 20. Secured directly beneath the shaft 19 is an extension 23 which receives a plate 21 on which a set of evenly-spaced needles 22 are mounted. The bottom diaphragm 18 cooperates with an intermediate diaphragm 18a to prevent coupling of a bending moment to the flexible diaphragm 16 as might be caused by inadvertent bending or twisting of the assembly as it is inserted into the meat.

When the center of the diaphragm 16 is deflected upwardly, the upper surface of its periphery is in compression. Proceeding radially toward the center, the compressive strains diminish to zero; and the strain on the upper surface is thereafter a tensile strain up to the center. The illustration of strain gauge placement is schematic, but we prefer to use four semi-conductor strain gauges placed along a common diameter of the flexible diaphragm 16 so that the two inner sensors measure tensile strain and the outer two sensors measure compressive strain in the diaphragm.

As the needles 22 penetrate the meat up to a point determined by the stop members 11, the center portion of the diaphragm 16 is deflected by an amount proportional to the resistive force of penetration. This deflection is then sensed by the compressive and tensile strains in the strain gauges 15 and reflected by a corresponding change in the resistance of these sensors.

The two strain sensors measuring compressive strain are located in diagonally-opposite branches of an electrical bridge circuit, described in greater detail within; and the other two sensors measuring tensile strain are located in the two remaining branches of the bridge circuit. For purposes of increasing the accuracy of the measuring strain gauges as they are placed in the bridge circuit, wire-wound calibration resistors located on terminal posts 24 within the housing 14 are connected in series with the supply terminals of the bridge circuit, as described in greater detail in connection with the circuit schematic diagram of FIG. 3. For present purposes, it will be realized that for no resistive force on the needles 22, the bridge circuit generates a zero output signal or a reference signal from which deviations may be measured to represent penetration resistance force.

Figure 2:
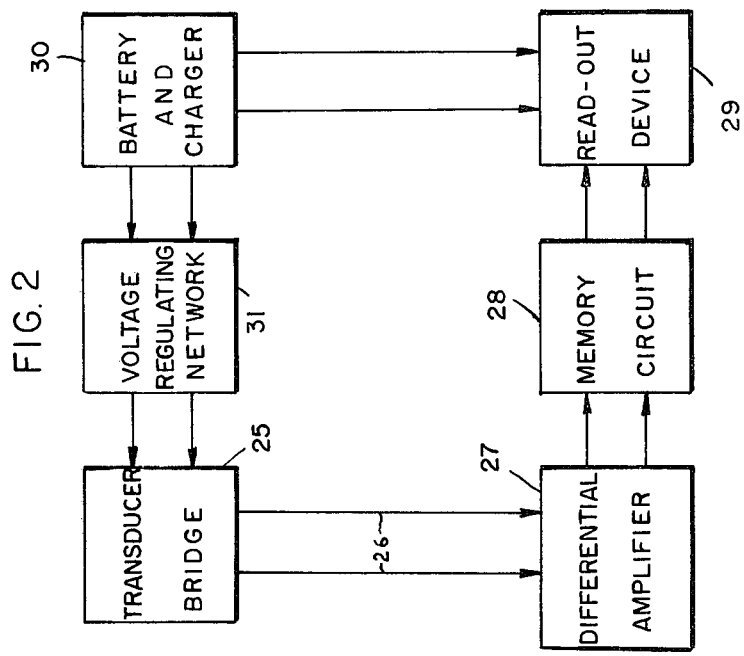
FIG. 2 is a schematic block diagram of an electrical system according to the present invention.

For purposes of understanding the present invention, it is deemed advisable at this time to describe a functional block diagram of the entire circuit schematic so that the function of each circuit element may be kept in mind during disclosure of the individual circuit elements. Turning then to FIG. 2, the transducer bridge, generally described above and more particularly described within, is schematically designated by the block 25; and it generates an output signal along lines 26, the instantaneous difference in potential between the lines 26 being representative of the instantaneous penetration resistive force encountered by the probe needles 22 during insertion.

The signal lines 26 are fed to the input of a differential amplifier 27 which is modified to amplify only those signals representative of the insertion force and to discriminate against signals of opposite polarity. The output of the difference amplifier 27 is coupled to a memory circuit 28 which includes a capacitor for storing charge. The capacitor, as described within, is fed by a circuit which permits current to flow only unidirectionally so that if the insertion of the probe is unsteady and for example, slows down for a short time so that the output signal from the transducer bridge 25 begins to diminish, the memory capacitor is cut off or disconnected from the output of the differential amplifier 27 during this period. Thus, if the force signal diminishes, charge is not drawn from the capacitor so that the accumulated charge on the memory capacitor in the memory circuit 28 is representative of the peak of the penetration resistive force encountered. The output of the memory circuit 28 is fed to a readout device 29 for displaying or recording the measurement.

A storage battery and charger circuit 30 is coupled through a voltage regulating network 31 to energize the transducer bridge 25 so that the entire system is portable and may be set up at different locations. The battery may be recharged; and the voltage regulating network 31 ensures the proper voltage level being fed to the resistive transducer bridge 25 so that operation is substantially independent not only of the charge state of the battery but also of the ambient temperature in which the system is being used. The battery and charger circuit 30 also contains a subtraction circuit so that the charge state of the supply battery may be read by means of the readout device 29, if it is a meter, on proper scale.

Figure 3:
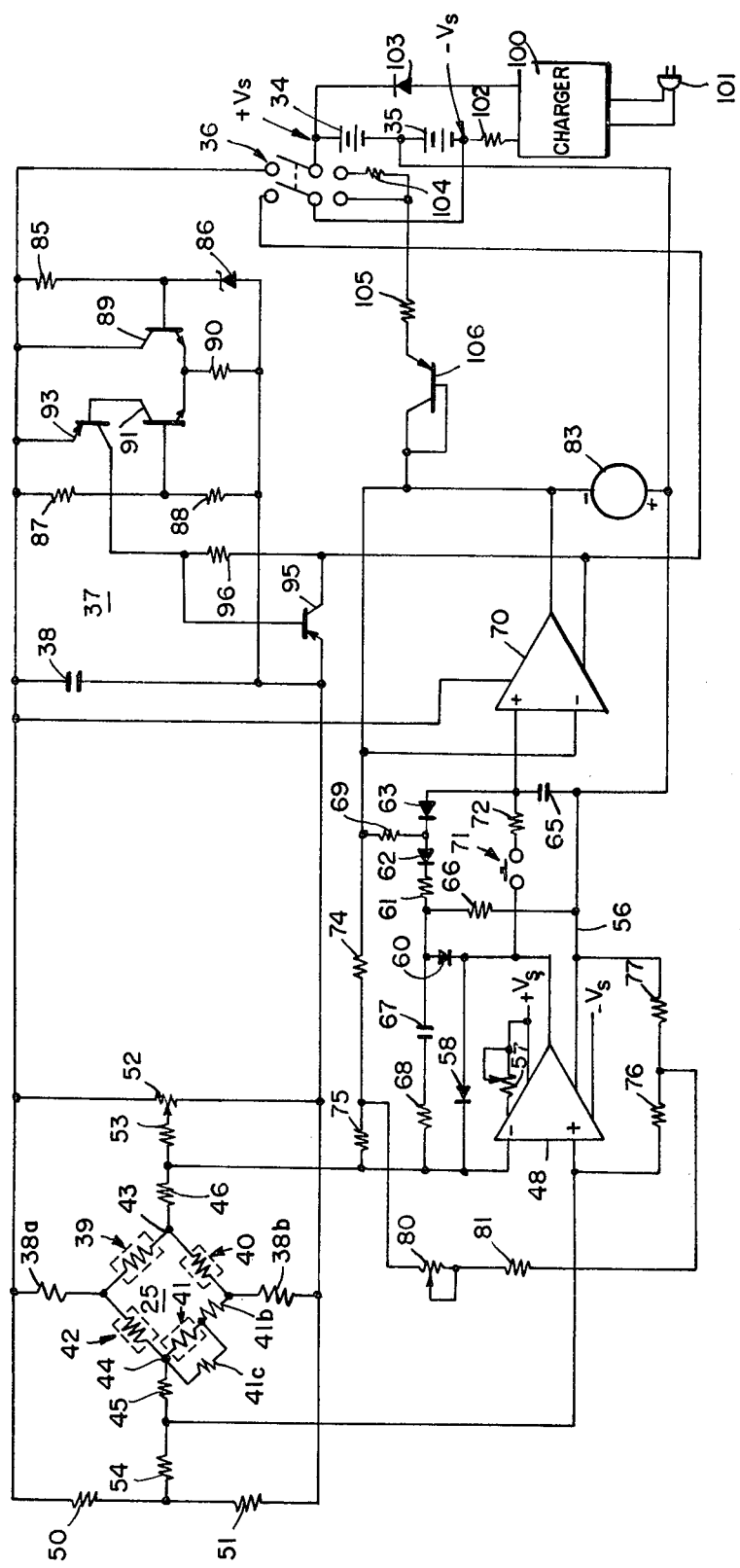
FIG. 3 is a detailed circuit schematic diagram of the system of FIG. 2.

Turning now to FIG. 3, there is seen a detailed circuit schematic diagram corresponding to the functional block schematic diagram just explained. First and second storage batteries 34 and 35 (see right hand side of FIG. 3) are connected in series to form the voltage supply for the circuit. The positive terminal of battery 34 and the negative terminal of battery 35 are connected respectively to first and second movable contacts of a switch generally designated 36 which can be seen to be a double-pole, double-throw switch.

The two supply voltages are coupled to a voltage regulator network generally designated by reference numeral 37 and explained in greater detail within. The output of the voltage regulator network 37 is connected across a filter capacitor 38 and to the supply nodes of the transducer bridge 25 by means of calibration resistors 38a and 38b. The calibration resistors cause the transducer bridge 25 to generate a specific output voltage for a given applied voltage. Thus, the resistors 38a and 38b adjust the voltage which appears at the excitation terminals to yield a desired output signal for a given applied force.

The individual strain gauges (one in each branch) are schematically illustrated at 39, 40, 41 and 42 respectively. Assuming for illustration that it has been determined that strain gauge 41 is the sensor with the highest temperature coefficient of resistance, a resistor 41c is connected in parallel with it. The parallel combination yields a net temperature coefficient of resistance that will minimize the no-load output change of the bridge with temperature. Because the inclusion of resistor 41c unbalances the bridge, a resistor 41b is connected in series with the aforementioned parallel combination to achieve a balance.

As has already been explained, two of the strain gauges preferably measure tensile strain while the other two measure compressive strain; and the two measuring tensile strain are in diagonally-opposite branches, for example 39 and 41 of the bridge circuit; and the two strain gauges measuring compressive strain are in the branches 40 and 42. Thus, there is developed across output nodes 43 and 44, a signal which is representative of the instantaneous penetration resistance force encountered by the probe during insertion. The double-ended output signal from the bridge 25 is then connected through resistors 45 and 46 respectively to the positive and negative input terminals of a differential amplifier 48. The amplifier 48 amplifies the signal received from the transducer bridge.

A zeroing network is provided for properly balancing the output of the transducer bridge to provide zero output at the measuring amplifiers for zero transducer force. This zeroing network includes first and second series-connected resistors 50 and 51 connected directly across the supply voltage and a variable potentiometer 52, the fixed terminals of which are connected across the supply voltage. The variable contact of the potentiometer 52 is connected through a resistor 53 to the resistor 46; and the junction between resistors 50 and 51 is connected to the resistor 45 by means of a resistor 54. The output of the transducer bridge 25 is then balanced by adjustment of the potentiometer 52 so that the readout signal indicates zero when the probe is at rest (i.e. for zero transducer force).

As indicated in the drawing, the positive supply voltage ($+V_s$), the negative supply voltage ($-V_s$) and the system common (represented by the line 56 and connected to the junction between the batteries 34 and 35) are all fed into the differential amplifier 48 for establishing bias as required. A potentiometer 57 provides a zero offset adjustment for the inverting amplifier 48.

The anode of a diode 58 is connected to the output of the amplifier 48, and the cathode of the diode 58 is connected to the negative input terminal of the amplifier 48. Thus, as long as the voltage on the positive input terminal of the differential amplifier is greater than the voltage on its negative terminal, the amplifier operates with its normal and constant gain; however, should the input voltage on the positive terminal become less than the voltage on its negative input terminal, the output voltage will become positive to forward-bias the diode 58 and thereby reduce the gain of the amplifier to zero.

A series circuit comprising a diode 60, resistor 61, and diodes 62 and 63 couple the output of the amplifier 48 to one terminal (hereinafter sometimes referred to as the signal terminal) of a storage capacitor 65, the other terminal of which is connected to the system common. It will be remembered that the normal output of the amplifier 48 is negative and that the diodes 60, 62 and 63 are arranged so that a negative output signal from the amplifier 48 will cause current to flow into the capacitor 65; however, a positive output voltage from the amplifier 48 will be blocked by means of these diodes. A resistor 66 is interconnected between the anode of diode 60 and the system common.

A feedback network including a capacitor 67 and a resistor 68 is connected between the anode of diode 60 and the negative input terminal of the amplifier 48. A resistor 69 is coupled between the system output signal terminal and the junction between diodes 62 and 63. The resistor 69 has a very large value of resistance (of the order of $10^7$ ohms); and it (together with resistor 66) provides a path for the leakage current through the diode 62.

The junction between the capacitor 65 and the anode of diode 63 is connected to the positive input terminal of a second operational amplifier 70, also connected to operate as a differential amplifier. The negative input terminal of amplifier 70 is connected directly to its output terminal. A push button switch 71, connected in series with a current-limiting resistor 72, couples the signal terminal of the capacitor 65 to the output of the differential amplifier 48 for selectively resetting the capacitor 65 by an operator after a measurement has been observed or recorded and after the transducer has been removed from the carcass. This provides the establishment of a reference level on the signal terminal of the storage capacitor which is equal to the output signal of the differential amplifier 48 prior to each measurement.

Feedback is achieved from the output of amplifier 70 to the input of amplifier 48 by means of resistors 74 and 75 which are connected in series between the negative terminal of the amplifiers 48 and the output of amplifier 70. Resistors 76 and 77 are connected between the positive input terminal of the amplifier 48 and the system common to establish a balanced input. The junction between resistors 74 and 75 is connected to the junction between the resistors 76 and 77 by means of a variable resistor 80 and a fixed resistor 81. Adjustment of the resistor 80 adjusts the gain of the amplifier 48; and it calibrates the entire read system so that the range in the output signal of the amplifier 48 is coextensive with the scale on a readout meter 83 which is connected between the output terminal of the amplifier 70 and the system common in the polarity shown.

The amplifier 70 is a very high input impedance differential amplifier; and it has a voltage gain of unity so that the system gain is defined by the gain of the amplifier 48 which, as just mentioned, is adjusted by means of the variable shunt resistor 80.

Turning now to the voltage regulating circuit, a resistor 85 is connected in series with a Zener diode 86 across the two supply terminals of the transducer bridge 25. The diode 86 conducts at a known voltage, less than the designed supply voltage for the bridge 25. Similarly, a series circuit consisting of resistors 87 and 88 is connected across the supply terminals of the transducer bridge 25. The junction between the resistor 85 and the Zener diode 86 is connected to the base of an amplifying transistor 89, the emitter of which is connected to the anode of the Zener diode 86 by means of a resistor 90. Similarly, the junction between the resistors 87 and 88 is connected to the base of an amplifying transistor 91, the emitter of which is connected directly to the emitter of the transistor 89.

The collector of the transistor 91 is connected to the base of a transistor 93, the emitter of which is connected to one terminal of the transducer bridge 25. It will be appreciated that transistors 89 and 91 are arranged to form a difference amplifier responsive to differences in the diagonal of a bridge circuit formed of resistors 85, 87 and 88 together with the Zener diode 86. The collector of the transistor 93 is connected to the base of a transistor 95 and to a resistor 96. Current supplied to the transducer bridge passes through the transistor 95; and it will be observed that the collector-emitter junction of the pass transistor 95 is interposed between the supply voltage and the transducer bridge.

The resistor 96 is also connected to the collector of the transistor 95; and the emitter of the transistor 95 is connected to one of the supply terminals of the transducer bridge 25. In operation, the values of the resistors 85, 87 and 88 are selected so that for a given desired voltage across the energized terminals of the transducer bridge 25, the fixed drop across the Zener diode 86 will equal the voltage drop across the resistor 88; and the difference amplifier formed by the transistors 89 and 91 cause a known current to flow in transistors 93 and 95 sufficient to drop a known, fixed voltage across the collector-emitter junction of transistor 95 and thus supply a known voltage to the transducer bridge. However, if the voltage across the energized terminals of the bridge 25 begins to decrease, the base of transistor 91 will become relatively negative with respect to the base of the transistor 89 (due to the decrease in voltage drop across the resistor 88 relative to the fixed voltage drop across the Zener diode 86). This decrease in voltage is sensed by the difference amplifier which then increases the current drawn from the base of the transistor 95 which decreases the collector-to-emitter voltage drop across the transistor 95 and thereby provides a greater voltage to the energized terminals of the bridge 25. Smoothing of the transition is achieved by means of the capacitor 38.

Turning now to the battery charger and indicator circuitry, the charge is conventional and generally designated by reference numeral 100; and it is equipped with a plug 101 for connecting into a 110 volt, 60 cycle supply, for example. One of the output terminals of the charger 100 is connected to the negative terminal of the battery 35 through a resistor 102; and the other terminal of the charger 100 is connected to the positive terminal of the battery 34 by means of a diode 103 with the cathode of the diode 103 connected to the positive terminal, as illustrated. When it is desired to check the charge condition of the batteries 34 and 35, the switch 36 may be thrown to the second position indicated wherein the full battery voltage appears across a load resistor 104. When the switch 36 is in this position, the negative terminal of the battery 35 is connected in series with a dropping resistor 105 and a transistor 106 having its collector and base connected together and coupled to the negative terminal of the meter 83. With the transistor 106 thus connected, a constant voltage drop occurs across its collector-to-emitter junction so that even though the meter 83 is designed to record a much lower voltage range (for example, 0–5 volts) than the total range of the supply by the batteries 34 and 35 (which may be 12-volt batteries), nevertheless by dropping a large portion of that voltage across the transistor 106, relatively small changes in total battery voltage will be displayed on the meter 83. Thus, the meter 83 can be used both to record or display the measure of tenderness of the meat, and to check the charge condition of the supply batteries within close limits.

In the selection of components, persons skilled in the art will perform such selection keeping in mind the functional requirement which has been described. For example, the memory capacitor will preferably have a minimum of leakage current. The diodes which unidirectionally feed the memory capacitor will also have a minimum of leakage current; the second operational amplifier will have a very high impedance so as to not load the memory capacitor, and so on.

In operation, the described circuit embodiment follows these general principles, namely that a signal is generated by a transducer bridge having an amplitude representative of instantaneous penetration resistance force encountered by a probe during insertion into a carcass. This force signal is then amplified by an operational differential amplifier, diode-bounded to amplify signals of only one polarity. The amplified output signal is still representative of instantaneous penetration resistance; and it is fed through a unidirectional currentconducting network which passes only those signals representative of an increase in the absolute value of the signal. Thus, this network discriminates against signals which are generated by temporary or even permanent decreases in force measurement. In other words, the unidirectional current conduction circuitry will not conduct until the output of the differential amplifier 48 exceeds the voltage stored on the storage capacitor 65. The current passing through this unidirectional conduction circuit flows through a capacitor. Thus incremental values of charge flow into the capacitor and are stored there for every incremental increase (but not decrease) in the penetration resistance force encountered. The total of such stored charges is thus representative of the peak of the penetration resistance force. The voltage across the capacitor (which is directly proportional to the charge stored thereby) is then coupled to a readout circuit, such as a voltage meter, by means of a second operational amplifier which has a high input impedance and unity voltage gain, and is non-inverting.

Having thus described in detail a preferred embodiment of a system for reading the peak resistive penetration force encountered by a probe inserted into raw meat together with a simplified embodiment of the measuring circuit, it will be appreciated that certain of the individual components and functional elements of the measuring system may be modified or equivalent circuits substituted without departing from the inventive principle; and it is, therefore, intended that all such modifications and substitutions be covered as they are embraced within the spirit and scope of the appended claims.

We claim:

1. A system for measuring the tenderness of meat upon cooking by non-destructive testing of raw meat comprising: a probe having a plurality of needles and a handle, said probe adapted to have said needles inserted directly into said meat by the hand of an operator; a flexible diaphragm mounted to said probe and adapted to deflect in response to the insertion of said needles; strain measuring means mounted on said diaphragm for generating a force signal representative of the penetration resistance force encountered as said needles are inserted in said meat; means receiving said force signal including storage means for storing a signal corresponding to the peak of said force signal; and output means receiving the signal stored in said storage means for converting said stored signal to an output signal representative of the tenderness of said meat.

2. The system of claim 1 wherein said flexible diaphragm is rigidly mounted about its periphery to said probe, and further including a shaft holding said needles and connected to the center of said diaphragm to cause deflection thereof when resistance is encountered by said probe, said strain measuring means mounted on said diaphragm for generating signals representative of the strain caused by deflection thereof when said probe is inserted in said meat; said system further including source means for supplying voltage to said strain measuring means thereby to generate said force signal representative of said deflection and of said penetration resistance force.

3. The system of claim 2 further comprising stop means mounted to said probe for limiting the travel of said diaphragm during insertion to thereby prevent overloading of said strain measuring means.

4. The system of claim 2 wherein said strain measuring means includes a plurality of strain gauges, a first of said strain gauges measuring compressive strain in said flexible diaphragm and a second of said strain gauges measuring tensile strain in said flexible diaphragm, said first and second strain gauges connected respectively in different branches of an electrical bridge circuit.

5. The system of claim 4 further comprising temperature compensating means in circuit with said electrical bridge circuit for generating a predetermined bridge output signal at zero strain in said gauges over a design temperature range.

6. The system of claim 4 wherein said strain gauges comprise four resistive strain gauges, a first pair of said strain gauges measuring compressive strain in said flexible diaphragm and disposed in a first set of opposite branches of a bridge circuit, a second pair of said strain gauges measuring tensile strain in said flexible diaphragm and disposed in a second set of opposite branches of said bridge circuit, said system further including voltage regulating means interposed between said source means and said bridge circuit for maintaining the supply voltage of said bridge circuit at a constant level over a predetermined range of voltage levels of said source means, whereby variations in the terminal voltage of said source means are not reflected in said force signal.

7. The system of claim 6 further comprising calibration means coupling said voltage regulating means with the energized terminals of said bridge circuit whereby said bridge circuit generates a predetermined output signal for a given applied voltage.

8. The system of claim 1 wherein said output means receiving said force signal comprises: amplifier means for amplifying said force signal; unidirectional current-conduction means for passing signals representative only of incremental increases in penetration resistance forces encountered during insertion of said probe and for blocking signals representative of decreasing resistance force; and capacitor means having a signal terminal receiving the signal conducted by said unidirectional current-conduction means for storing charge representative of the sum of said incremental increases in said force signal and thereby storing a signal representative of the peak signal passing through said unidirectional current-conduction means.

9. The system of claim 8 further comprising reset switch means for selectively connecting said signal terminal of said capacitor means to the output terminal of said amplifier means to discharge said capacitor to the signal level of the output of said amplifier after a measurement has been made.

10. A system for measuring the tenderness of meat comprising: a probe including handle means for holding by an operator and stop means secured to said handle means and provided with stop members; means including a plurality of spacedapart needles connected to said handle means for penetrating said meat; said stop members being located adjacent said needles and intermediate the ends thereof to engage said meat during penetration and to thereby limit the depth of penetration of said needles; transducer means responsive to resistance forces encountered by said needles for generating an electrical signal representative of the instantaneous penetration resistance force, said transducer means including a flexible diaphragm secured about its periphery to said handle means and secured at its center to said needle means, and resistive strain measuring means on said flexible diaphragm for generating a force signal; electrical means receiving said electrical force signal of said transducer means for storing the peak value thereof, said peak value being representative of the maximum resistance force encountered as said needles penetrate said meat.

11. The combination of claim 10 further comprising limit means attached to said handle for limiting the deflection of said flexible member when said needles are inserted in said probe.

12. The combination of claim 10 further comprising second and third spaced-apart diaphragms connected at their peripheries to said housing and rigidly coupled at their centers to said needle means for preventing the coupling of bending moments from said needle means to said flexible diaphragm.

13. In a system for measuring the tenderness of meat, the combination comprising penetration means including a probe carrying a plurality of pointed needles and adapted for penetrating said meats by force of hand and a deflectable diaphragm supported by said probe and having its center connected to said needles for deflection by said needles when the same are inserted in the meat; first circuit means associated with said penetration means for generating an electrical signal representative of the penetration resistance force encountered by said needles during insertion into said meat; second circuit means receiving said electrical signal representative of penetration resistance force for generating and retaining a signal representative of the maximum penetration resistance force during one insertion stroke of said penetration means; and reset circuit means for selectively resetting said second circuit means after a penetration stroke is completed.

14. A portable direct read out system for measuring tenderness of cooked meat by testing the meat when raw comprising a hand probe having a plurality of pointed needles for penetrating the raw meat under hand force of an operator, said probe including mounting means for mounting said needles in laterally spaced relation, handle means including a housing, a shaft connected to said needles, a deflectable diaphragm secured about its periphery to the housing and connected at its center to said shaft; electrical transducer means includes resistive strain gauge means mounted on a surface of said diaphragm and varying in electrical resistance in accordance with strain induced on said surface when said diaphragm is deflected by said shaft for generating a signal representative of the instantaneous penetration resistance force on said needles during insertion into said meat; electrical storage circuit means receiving said electrical signal of said transducer means for storing an electrical signal representative of the peak penetration resistance signal generated by said transducer means, and portable electrical energy storage means capable of being carried by an operator along with said probe for supplying electrical energy to said transducer means.

15. A hand-actuatable probe for use in testing tenderness of raw meat comprising a handle engageable by an operator for holding and moving the probe; a housing rigidly connected to said handle; a first deflectable diaphragm secured about its periphery to the interior of said housing; shaft means engaging said diaphragm for deflecting the same when urged against it; a plurality of pointed needles spaced apart from each other and in parallel relation; means for connecting said needles to said shaft means to couple movement of said needles relative to said housing to said diaphragm; second and third diaphragms connecting said shaft means to said housing for preventing twisting of said shaft relative to said housing as said needles are inserted; first stop means connected to said handle for engaging the meat during insertion to limit the penetration depth of said needles to a predetermined amount whereby any further insertion force is transmitted to said handle and not to said diaphragm; second stop means for limiting the extent of travel of said shaft and diaphragm to protect against overload; and electrical resistive strain gauge means measuring strain in a surface of said diaphragm produced by deflection of said diaphragm when said needles penetrate said meat.

* * * * *